(12) United States Patent
Haile

(10) Patent No.: US 9,023,326 B2
(45) Date of Patent: May 5, 2015

(54) COMPOSITIONS FOR REMOVABLE GEL APPLICATIONS FOR NAILS AND METHODS OF THEIR USE

(75) Inventor: Danny Lee Haile, La Mirada, CA (US)

(73) Assignee: Nail Alliance LLC, Gladstone, MO (US)

( * ) Notice: Subject to any disclaimer, the term of this patent is extended or adjusted under 35 U.S.C. 154(b) by 224 days.

(21) Appl. No.: 13/383,348

(22) PCT Filed: Jul. 19, 2010

(86) PCT No.: PCT/US2010/042395
§ 371 (c)(1),
(2), (4) Date: Jan. 10, 2012

(87) PCT Pub. No.: WO2011/011304
PCT Pub. Date: Jan. 27, 2011

(65) Prior Publication Data
US 2012/0118314 A1 May 17, 2012

Related U.S. Application Data

(60) Provisional application No. 61/346,949, filed on May 21, 2010, provisional application No. 61/260,700, filed on Nov. 12, 2009, provisional application No. 61/227,257, filed on Jul. 21, 2009.

(51) Int. Cl.
| | |
|---|---|
| *A61Q 3/02* | (2006.01) |
| *A61K 8/81* | (2006.01) |
| *A45D 34/04* | (2006.01) |
| *A61K 8/35* | (2006.01) |
| *A61K 8/37* | (2006.01) |
| *A61K 8/40* | (2006.01) |
| *A61K 8/73* | (2006.01) |
| *A61K 8/891* | (2006.01) |
| *A45D 29/12* | (2006.01) |

(52) U.S. Cl.
CPC ............ *A61K 8/8147* (2013.01); *A45D 34/045* (2013.01); *A61K 8/35* (2013.01); *A61K 8/37* (2013.01); *A61K 8/375* (2013.01); *A61K 8/40* (2013.01); *A61K 8/731* (2013.01); *A61K 8/891* (2013.01); *A61K 2800/24* (2013.01); *A61Q 3/02* (2013.01); *A45D 29/12* (2013.01); *A61K 8/8164* (2013.01)

(58) Field of Classification Search
None
See application file for complete search history.

(56) References Cited

U.S. PATENT DOCUMENTS

| | | | |
|---|---|---|---|
| 2,979,061 A | 4/1961 | Greenman et al. | |
| 3,629,187 A | 12/1971 | Waller | |
| 3,709,866 A | 1/1973 | Waller | |
| 3,928,113 A | 12/1975 | Rosenberg | |
| 4,089,763 A | 5/1978 | Dart et al. | |
| 4,174,307 A | 11/1979 | Rowe | |
| 4,189,365 A | 2/1980 | Schmitt et al. | |
| 4,229,431 A | 10/1980 | Lee, Jr. et al. | |
| 4,260,701 A | 4/1981 | Lee, Jr. | |
| 4,302,561 A | 11/1981 | Becher et al. | |
| 4,302,562 A | 11/1981 | Becher et al. | |
| 4,303,764 A | 12/1981 | Becher et al. | |
| 4,374,209 A | 2/1983 | Rowlands | |
| 4,421,881 A | 12/1983 | Benkendorf et al. | |
| 4,528,333 A | 7/1985 | Chang et al. | |
| 4,544,625 A | 10/1985 | Ishimaru et al. | |
| 4,600,030 A | 7/1986 | Newman | |
| 4,666,952 A | 5/1987 | Henne et al. | |
| 4,669,491 A * | 6/1987 | Weisberg et al. | 132/73 |
| 4,682,612 A | 7/1987 | Giuliano | |
| 4,690,369 A | 9/1987 | Giuliano | |
| 4,704,303 A | 11/1987 | Cornell | |
| 4,718,957 A | 1/1988 | Sensenbrenner | |
| 4,721,735 A | 1/1988 | Bennett et al. | |
| 4,745,003 A | 5/1988 | Sirkoch et al. | |
| 4,747,419 A | 5/1988 | Flynn et al. | |
| 4,766,005 A | 8/1988 | Montgomery et al. | |
| 4,775,580 A | 10/1988 | Dighton | |
| 4,813,875 A | 3/1989 | Hare | |
| 4,844,102 A | 7/1989 | Repensek et al. | |
| 4,846,165 A | 7/1989 | Hare et al. | |
| 4,855,184 A | 8/1989 | Klun et al. | |
| 4,863,993 A | 9/1989 | Montgomery | |
| 4,867,680 A | 9/1989 | Hare et al. | |
| 4,971,837 A | 11/1990 | Martz et al. | |
| 4,975,488 A | 12/1990 | Furukawa et al. | |
| 4,985,516 A | 1/1991 | Sakashita et al. | |
| 5,071,888 A | 12/1991 | Kubota | |

(Continued)

FOREIGN PATENT DOCUMENTS

| | | |
|---|---|---|
| EP | 0426085 | 10/1990 |
| EP | 453628 | 10/1991 |

(Continued)

OTHER PUBLICATIONS

International Search report for PCT/US2010/042395 filed Jul. 19, 2010 mailed Jan. 24, 2011.

(Continued)

*Primary Examiner* — Peter J Reddig
*Assistant Examiner* — Sarah Chickos
(74) *Attorney, Agent, or Firm* — Feldman Gale, P.A.; Walter C. Frank

(57) ABSTRACT

Novel radiation curable gel-based mammalian nail coating compositions, kits containing these compositions, and methods of their use are disclosed. The novel compositions and/or kits are useful, inter alia, for providing durable, "soak-off" type nail coatings.

17 Claims, No Drawings

(56) References Cited

U.S. PATENT DOCUMENTS

| | | | |
|---|---|---|---|
| 5,118,495 A | 6/1992 | Nafziger et al. | |
| 5,127,414 A | 7/1992 | Mast et al. | |
| 5,133,966 A | 7/1992 | Khamis | |
| 5,177,120 A | 1/1993 | Hare et al. | |
| 5,229,431 A | 7/1993 | Pinchuk | |
| 5,319,011 A | 6/1994 | Schoon | |
| 5,330,750 A * | 7/1994 | Sheard et al. | 424/61 |
| 5,334,455 A | 8/1994 | Noren et al. | |
| 5,344,583 A | 9/1994 | Bayless | |
| 5,407,666 A | 4/1995 | Patel et al. | |
| 5,415,903 A | 5/1995 | Hoffman et al. | |
| 5,450,864 A | 9/1995 | LaJoie et al. | |
| 5,453,450 A | 9/1995 | Kinzer et al. | |
| 5,453,451 A | 9/1995 | Sokol | |
| 5,456,905 A | 10/1995 | Valenty | |
| 5,516,509 A | 5/1996 | Marr-Leisy et al. | |
| 5,523,076 A | 6/1996 | Schoon | |
| 5,599,622 A | 2/1997 | Kinzer et al. | |
| 5,637,292 A * | 6/1997 | Thomas | 424/61 |
| 5,662,891 A | 9/1997 | Martin | |
| 5,708,052 A | 1/1998 | Fischer et al. | |
| 5,763,503 A | 6/1998 | Cowperthwaite et al. | |
| 5,785,958 A | 7/1998 | Sirdesai et al. | |
| 5,792,447 A | 8/1998 | Socci et al. | |
| 5,824,373 A | 10/1998 | Biller et al. | |
| 5,830,442 A | 11/1998 | Beaver | |
| 5,882,636 A | 3/1999 | Mui et al. | |
| 5,965,111 A | 10/1999 | Ellingson et al. | |
| 5,965,147 A | 10/1999 | Steffier | |
| 5,985,951 A | 11/1999 | Cook | |
| 5,985,998 A | 11/1999 | Sommerfeld et al. | |
| 6,015,549 A | 1/2000 | Cowperthwaite et al. | |
| 6,020,402 A | 2/2000 | Anand et al. | |
| 6,031,046 A | 2/2000 | Smith | |
| 6,051,242 A | 4/2000 | Patel et al. | |
| 6,080,389 A | 6/2000 | Sheariss et al. | |
| 6,080,414 A | 6/2000 | Smith, III et al. | |
| 6,100,097 A | 8/2000 | Sirdesai et al. | |
| 6,123,931 A | 9/2000 | Ellingson et al. | |
| 6,136,300 A | 10/2000 | Ellingson et al. | |
| 6,147,137 A | 11/2000 | Jia | |
| 6,156,325 A | 12/2000 | Farer et al. | |
| 6,174,634 B1 | 1/2001 | De Bastiani | |
| 6,228,433 B1 | 5/2001 | Witt | |
| 6,244,274 B1 | 6/2001 | Sirdesai et al. | |
| 6,262,296 B1 | 7/2001 | Nomura et al. | |
| 6,270,751 B1 | 8/2001 | Resler | |
| 6,306,375 B1 | 10/2001 | Ellingson et al. | |
| 6,332,291 B1 | 12/2001 | Flosbach et al. | |
| 6,335,060 B1 | 1/2002 | Inoue | |
| 6,391,938 B1 | 5/2002 | Lilley | |
| 6,455,033 B1 | 9/2002 | Steffier | |
| 6,481,444 B1 | 11/2002 | Lilley | |
| 6,489,396 B2 | 12/2002 | Nakamura et al. | |
| 6,537,530 B2 | 3/2003 | Mui et al. | |
| 6,555,096 B2 | 4/2003 | Carrion et al. | |
| 6,593,395 B2 | 7/2003 | Angeletakis et al. | |
| 6,599,958 B2 | 7/2003 | Lilley | |
| 6,616,920 B1 | 9/2003 | Ito et al. | |
| 6,656,483 B1 | 12/2003 | Farer et al. | |
| 6,713,551 B2 | 3/2004 | Takahashi et al. | |
| 6,767,987 B2 | 7/2004 | Okazaki | |
| 6,803,394 B2 | 10/2004 | Lilley et al. | |
| 6,818,207 B1 | 11/2004 | Schoon et al. | |
| 7,025,954 B2 | 4/2006 | Johnston | |
| 7,151,130 B2 | 12/2006 | Bremser et al. | |
| 7,261,926 B2 | 8/2007 | Schwarte et al. | |
| 8,124,058 B2 | 2/2012 | Schoon et al. | |
| 8,263,677 B2 | 9/2012 | Conger et al. | |
| 2002/0102222 A1 | 8/2002 | Carrion et al. | |
| 2003/0019501 A1 | 1/2003 | Hirota et al. | |
| 2003/0220416 A1 | 11/2003 | Montgomery et al. | |
| 2004/0180213 A1 * | 9/2004 | Harris et al. | 428/423.1 |
| 2005/0065297 A1 | 3/2005 | Patel | |
| 2006/0039939 A1 | 2/2006 | Lai et al. | |
| 2006/0134032 A1 * | 6/2006 | Ilekti et al. | 424/61 |
| 2006/0198890 A1 | 9/2006 | Steffier et al. | |
| 2006/0283720 A1 | 12/2006 | Minnella | |
| 2007/0043728 A1 * | 2/2007 | Chan et al. | 707/9 |
| 2007/0286827 A1 | 12/2007 | Sheariss et al. | |
| 2008/0081054 A1 * | 4/2008 | Ilekti | 424/401 |
| 2008/0159973 A1 | 7/2008 | Doan | |
| 2008/0226573 A1 | 9/2008 | Schoon et al. | |
| 2008/0241083 A1 | 10/2008 | Schoon et al. | |
| 2010/0008876 A1 | 1/2010 | Tanaka et al. | |
| 2010/0143274 A1 * | 6/2010 | Deshayes et al. | 424/59 |
| 2010/0160557 A1 | 6/2010 | Murofushi et al. | |
| 2011/0060065 A1 | 3/2011 | Vu et al. | |
| 2011/0077334 A1 | 3/2011 | Oi et al. | |
| 2011/0081306 A1 | 4/2011 | Vu et al. | |
| 2011/0082228 A1 | 4/2011 | Vu | |
| 2011/0182838 A1 | 7/2011 | Vu et al. | |
| 2011/0226271 A1 | 9/2011 | Raney et al. | |
| 2011/0274633 A1 | 11/2011 | Vu et al. | |
| 2012/0083547 A1 | 4/2012 | Vu et al. | |

FOREIGN PATENT DOCUMENTS

| | | |
|---|---|---|
| EP | 0453628 | 10/1991 |
| EP | 1067898 | 5/2006 |
| WO | WO 98/48769 | 11/1998 |
| WO | WO 01/29108 | 4/2001 |
| WO | WO 01/43579 | 6/2001 |
| WO | WO 2007/043728 * | 4/2007 |
| WO | WO 2011/011304 | 1/2011 |

OTHER PUBLICATIONS

International Preliminary Report on Patentability for PCT/US2010/042395 filed Jul. 19, 2010 issued Jan. 24, 2011.

Written Opinion of the International Searching Authority for PCT/US2010/042395 filed Jul. 19, 2010 mailed Jan. 24, 2011.

Princess Nail Co. Ltd.; "Easy Off UV Gel;" Oct. 14, 2006; http://www.tradekey.com/product-free/Easy-Off-Uv-Gel-120992.html.

"Mini Manucure To-Go Set;" Jun. 2005.

"Ingredients;" Escona Online Shop; Nov. 24, 2010; http://www.escona.de/inhaltsstoffe.php?osCsid=4d20f490cfb1c308bbd5f2bbb26b4dba.

Nails DeLuxe; "Nails DeLuxe;" Nov. 24, 2010; http://www.nails-deluxe.eu/product_info.php?info=p1341_WHITE-CROSSES-JPN-1.html.

Office Action dated Sep. 22, 2014 for Russian Application No. 2012122608 filed Jul. 19, 2010.

Material Safety Data Sheet, "Crystal Nails Easy Off Color Gels", MSDS#: KIG122707-EOB, http://www.crystalnails4u.co.uk/msds/easy-off-color.pad, Dec. 8, 2008, pp. 1-7.

Material Safety Data Sheet, "Crystal Nails Easy Off", MSDS#: KIG082406-SKS, http://www.crystalnails4u.co.uk/msds/easy-off-color.pad, Sep. 26, 2006, pp. 1-5.

* cited by examiner

COMPOSITIONS FOR REMOVABLE GEL APPLICATIONS FOR NAILS AND METHODS OF THEIR USE

CROSS REFERENCE TO RELATED APPLICATIONS

This application claims the benefit of International Application No. PCT/US2010/42395 filed Jul. 19, 2010, U.S. Provisional Application No. 61/227,257 filed Jul. 21, 2009, U.S. Provisional Application No. 61/260,700 filed Nov. 12, 2009, and U.S. Provisional Application No. 61/346,949 filed May 21, 2010, the disclosures of which are hereby incorporated herein by reference in their entireties.

FIELD OF THE INVENTION

The present invention relates to radiation curable mammalian nail coating compositions, kits containing these compositions, and methods of their use. The present invention also relates to methods for the preparation of removable gel-based nail coating compositions.

BACKGROUND OF THE INVENTION

Consumers use nail coatings to cosmetically enhance the appearance of their nails or protect the nails from the abuses found in their everyday environment. However, nail coating compositions typically lack the durability desired by consumers or are difficult to apply or remove in terms of time and/or effort. The lack of durability is often evidenced by a chipping or peeling of the coating soon after the original coating has been applied, requiring at least in part a reapplication of the coating in an attempt to recreate the aesthetic appearance or the therapeutic benefits of the original nail coating.

Lilley (U.S. Pat. Nos. 6,391,938, 6,803,394 and 6,599,958) discloses light cured nail coatings that are applied to natural nails and/or artificial nail tips for cosmetic purposes.

Ellingson et al. (U.S. Pat. No. 6,306,375) discloses long wear nail polish compositions having defined surface properties, as well as kits, films and methods of their use.

Ellingson et al. (U.S. Pat. No. 6,123,931) discloses polyurethane and polyacryl nail polish compositions useful as coatings for mammalian nails as well as methods of their use.

Ellingson et al. (U.S. Pat. No. 6,136,300) discloses long wear nail polish compositions having adhesion, toughness and hardness characteristics useful as coatings for mammalian nails as well as methods of their use.

Smith III et al. (U.S. Pat. No. 6,080,414) discloses films and kits useful as polishes for mammalian nails and methods of their use, reportedly having long wear characteristics.

Farer et al. (U.S. Pat. No. 6,656,483) discloses cosmetic compositions containing polyurethane for application to the skin and nails.

Farer et al (U.S. Pat. No. 6,156,325) and Carrion et al, (U.S. Pat. No. 6,555,096 and related published US Patent Application No. 2002/0102222) disclose nail enamel compositions containing a urea-modified thixotropic agent.

Sirdesai et al. discloses a polymerizable thixotropic oligomeric composition for sculpting artificial fingernails which is non-yellowing, and which maintains its shape when formed and polymerizes rapidly under actinic radiation.

Traditional nail coatings generally include two varieties: polish type, which cure by solvent evaporation, and polymer type, which cure by chemical reaction. Polymer type materials include, for example, powder/liquid systems and gel systems.

Gel systems, in contrast to the traditional polish and other polymer-type systems, particularly ultraviolet-cured gel systems, often comprise a gel that may be brushed onto the nails, cured, and shaped to create lifelike artificial nails. As compared with traditional polishes or other non-gel polymer-type systems, gel systems are relatively easy to use, are applicable in less time, are lightweight on the nail, have no odor (or only minimal odor), are durable, and have a high quality shine.

While thicker nail coatings may in general be more desirable due to their richer color and/or greater durability of the finished nail coating, it can be challenging to reasonably rapidly and substantially cure the entirety of the coating after its application. This is especially true for thicker and/or more highly pigmented UV-curable gel-based nail coating systems. This may be due, in part, to the nature of these coatings. For example, while UV light may readily penetrate the outermost regions of the coating composition to initiate the cure, the higher levels and/or darker hues of certain pigments in some coating compositions may limit penetration of the UV radiation into the innermost regions of the applied gel coating composition and thus increase the time required to substantially cure the entirety of the coating.

Often there is also a trade off in the choice of nail coatings between a particular coating's durability and its ease of removal. For example, some prior art gel coating compositions, while durable, cannot be readily removed by typical "soak-off" procedures and require a more laborious removal process. Alternatively, while some prior art gel coating compositions are very easily removed; those properties may lead to premature chipping and/or peeling of the coating, requiring additional maintenance or reapplication to stabilize the coating's overall appearance.

Thus, there is a real need in the art for gel systems that can be formulated to provide durable curable nail coatings, especially those capable of being removed relatively easily by "soak-off" procedures. There is also a need for gel systems that are capable of being applied easily and/or in less time than typically required by prior art gel systems or polishes. Further, there is a need for gel systems that provide such coatings regardless of the required coating color while providing a richness of color throughout the nail coating. Such gel coatings may give a more appealing and defect free appearance. The present invention is directed to these and other important ends.

SUMMARY OF THE INVENTION

Accordingly, the present invention is directed, in part, to radiation curable gel nail coating compositions, comprising:
  from about 40% to about 60% by weight of di-[hydroxyethyl methacrylic]trimethylhexyl dicarbamate based on the weight of the nail coating composition;
  from about 3% to about 5% by weight of at least one methacrylic acid ester based on the weight of the nail coating composition;
  from about 3% to about 6% by weight hydroxyethyl methacrylate based on the weight of the nail coating composition;
  from about 3% to about 6% by weight hydroxypropyl methacrylate based on the weight of the nail coating composition
  from about 0.1% to about 0.4% by weight of a photoinitiator based on the weight of the nail coating composition; and
  a pigmented nail lacquer.

In other embodiments, the present invention is directed in part to radiation curable gel nail coating compositions, comprising:
- from about 40% to about 60% by weight of di-[hydroxyethyl methacrylic]trimethylhexyl dicarbamate based on the weight of the nail coating composition;
- from about 3% to about 5% by weight of at least one methacrylic acid ester based on the weight of the nail coating composition;
- from about 3% to about 6% by weight hydroxyethyl methacrylate based on the weight of the nail coating composition;
- from about 3% to about 6% by weight hydroxypropyl methacrylate based on the weight of the nail coating composition;
- from about 0.1% to about 0.4% by weight of a photoinitiator based on the weight of the nail coating composition; and
- a nail art paint.

In other embodiments, the present invention is directed in part to radiation curable gel nail coating compositions, comprising:
- from about 40% to about 60% by weight of di-[hydroxyethyl methacrylic]trimethylhexyl dicarbamate based on the weight of the nail coating composition;
- from about 3% to about 6% by weight of a methacrylic acid ester based on the weight of the nail coating composition;
- from about 2% to about 6% by weight hydroxyethyl methacrylate based on the weight of the nail coating composition;
- from about 2% to about 6% by weight hydroxypropyl methacrylate based on the weight of the nail coating composition;
- from about 0.1% to about 1% by weight of a photoinitiator based on the weight of the nail coating composition; and
- from about 25 to about 40% by weight of a nail art paint based on the weight of the nail coating composition.

In certain other embodiments, the present invention is directed to kits suitable for coating mammalian nails with a radiation curable gel nail coating composition, comprising:
- a radiation curable gel nail coating composition of the present invention; and
- a bottle designed to substantially exclude the passage of UV light.

In some embodiments, the present invention is directed to methods of coating mammalian nails with a UV radiation curable gel nail coating composition, wherein the method comprises:
- applying a nail coating composition according to the present invention contiguously to a mammalian nail; and
- radiation-curing the composition on the nail.

DETAILED DESCRIPTION OF THE PREFERRED EMBODIMENTS

As used herein, the term "non-aqueous gel composition" refers to a gel composition having no more than a de minimis quantity of water.

As used herein, "alkylene" refers to a saturated straight chain or branched hydrocarbon diradical having from about 2 to about 15 carbon atoms (and all combinations and subcombinations of ranges and specific numbers of carbon atoms therein), preferably with from about 4 to about 12, more preferably 6 to about 10, yet more preferably about 7 to about 9, with about 8 to about 9 carbon atoms being most preferred. Alkylene groups include, but are not limited to, ethylene, n-propylene, methylethylene, dimethylmethylene, n-butylene, isobutylene, dimethylethylene, methylpropylene, ethylethylene, n-pentylene, isopentylene, neopentylene, trimethylethylene, dimethylpropylene, methylbutylene, ethylpropylene, n-hexylene, isohexylene, neo-hexylene, methylpentylene, dimethylbutylene, and trimethylpropylene, methylethylpropylene, n-heptylene, isoheptylene, neo-heptylene, dimethylpentylene, ethylpentylene, trimethylbutylene, methylethylbutylene, n-octylene, isooctylene, neo-octylene, methyl heptylene, dimethylhexylene, trimethylpentylene, methylethylpentylene, n-nonylene, isononylene, neo-nonylene, methyloctylene, dimethylheptylene, trimethylhexylene, methylethylhexylene, trimethylheptylene, methylethylheptylene, n-decylene, isodecylene, neo-decylene, methylnonylene, dimethyloctylene, trimethylheptylene, methylethylheptylene, trimethyloctylene, methylethyloctylene, and tetramethylhexylene.

As used herein, "polyurethane acrylate oligomer" refers to polyurethane oligomers wherein the acrylate portion of the oligomer is derived from one or more hydroxyalkylacrylic acid esters or hydroxyalkylmethacrylic acid esters, preferably hydroxyalkylmethacrylic acid esters. Non-limiting examples of hydroxyalkylmethacrylic acid esters include hydroxyethylmethacrylic acid ester and hydroxypropylmethacrylic acid ester.

The compositions, kits containing such compositions, and methods of use for such compositions and/or kits of the present invention are directed in part to meet a need in the industry for colored, preferably highly pigmented, gel-based coating compositions with improved properties as compared to prior art nail coatings. Thus, in certain embodiments, the present invention provides gel-based nail coating compositions that are removable using typical "soak-off" procedures, i.e., compositions that may be broken down and removed with solvents readily available for such purpose, including for example, acetone and/or other ketones, short chain alcohols, such as isopropanol, diacetone alcohol, $C_1$-$C_8$ alcohols, and the like, acrylic removers, tip removers, and/or various other acetate solvents, or any combination thereof.

In certain other embodiments, the compositions of the present invention may be cured by any process that may be incorporated into the composition which provides a free radical source capable of curing the nail coating compositions, so long as the resultant compositions may be safely employed and applied. This includes for example, any thermochemically or photochemically induced free radical processes as well as those employing catalysts to initiate the generation of free radicals and hence the curing of the nail coating composition that are known to the ordinarily skilled artisan.

In some preferred embodiments, typical compositions of the present invention comprise a combination of a gel base and a pigmented lacquer (i.e., nail polish), or the components of each thereof, that is activated and hardened under ultraviolet ("UV") light. Alternatively, typical compositions of the present invention comprise a combination of a gel base and a more heavily pigmented nail art paint, or the components of each thereof, that is activated and hardened under ultraviolet ("UV") light.

Any UV single or multiple light emitting source is contemplated herein by the inventor. The UV light source is not critical so long as the light source is a UV spectrum range light emitter and the power of such single or multiple light source is sufficient to activate and/or harden (i.e., cure) the nail coating composition in a desirable time. Typical lights may include UV light bulb sources and/or light emitting diode ("LED") lights, or any other equivalent light source, or any combination thereof. Typical lights may include UV light bulb sources and/or light emitting diode ("LED") lights, or any other equivalent light source, or any combination thereof.

In other embodiments, the compositions of the present invention may be applied in analogous fashion to typical prior art polishes, such as by brush application.

In some embodiments, the compositions of the present invention may be applied and set or cure the nail gel to final product coating in less time, preferably at least about 5, 10, 20, 30, 40, and even up to about 50% less than the time required to apply and/or set known nail gels.

Thus, in certain embodiments, compositions, kits containing such compositions, and methods of use for such compositions and/or kits of the present invention provide nail coatings that have the qualities of a nail polish with at least some, and preferably many of the benefits of a gel application. Benefits of certain embodiments of the present invention may include, but are not limited to easier application of the nail coating compositions, shorter manufacturing mix times of up to about 10, 20, 30, 40, 50, 60 or even 70% less mixing time than those for known polishes or gels, and/or faster or easier removal of the cured nail coating after use.

Users may further benefit from natural nail enhancement and reinforcement found in certain of the compositions of the present invention's embodiments. In some embodiments, the compositions of the present invention provide coatings that allow their removal in up to about 10, 20, 30, 40, or even up to about 50% percent less time than current polishes, gels, or similar products.

In other embodiments, the compositions, kits containing such compositions, and or methods employing such compositions and/or kits of the present invention provide coatings that may provide a harder and/or less brittle finish, more durability, and/or better nail coverage than prior art coatings. In some embodiments, complete coverage may be obtained with two applications of the coating.

In other embodiments of the present invention, the compositions and/or kits containing such compositions are provided as a bottle application, and in yet other embodiments of the present invention the compositions and/or kits containing such compositions are provided as a brush application.

The compositions, kits containing such compositions, and methods of use for such compositions and/or kits of the present invention may offer other further advantages as compared to currently available ultraviolet-cured gel products that are currently available. For example, in some embodiments of the present invention, the compositions are contained in bottles designed to substantially exclude UV light to deter activation of the formula by outside light during storage. The materials used to construct bottles designed to hold the nail coating compositions of the present invention may inherently exclude such light in certain embodiments. Alternately, other bottles not possessing these characteristics, including, for example, clear bottles, may be finished or coated with, for example, one or more special UV-protective coatings, including clear coatings. Either of these bottle alternatives may enable more of the nail gel to be used by the end user, for example, by reducing the level of inadvertent activation of the gel contained in the bottle prior to its application. In some instances this may allow substantially all of the product to be used for its intended purpose. A further advantage of providing the compositions in a clear-coated bottle is that the ultimate customer may then have a more ready ability to see and/or select the desired gel nail coating composition color. This is contrasted to existing ultraviolet-cured gel products that are traditionally provided in an opaquely colored white or black jar, which denies the customer an ability to see the actual color of the nail coating composition.

Accordingly, the present invention is directed, in part, to radiation curable gel nail coating compositions, comprising:
from about 40% to about 60% by weight of di-[hydroxyethyl methacrylic]trimethylhexyl dicarbamate based on the weight of the nail coating composition;
from about 3% to about 5% by weight of at least one methacrylic acid ester based on the weight of the nail coating composition;
from about 3% to about 6% by weight hydroxyethyl methacrylate based on the weight of the nail coating composition;
from about 3% to about 6% by weight hydroxypropyl methacrylate based on the weight of the nail coating composition;
from about 0.1% to about 0.4% by weight of a photoinitiator based on the weight of the nail coating composition; and
a pigmented nail lacquer.

In other embodiments, the present invention is directed, in part, to radiation curable gel nail coating compositions, comprising:
from about 40% to about 60% by weight of di-[hydroxyethyl methacrylic]trimethylhexyl dicarbamate based on the weight of the nail coating composition;
from about 3% to about 5% by weight of at least one methacrylic acid ester based on the weight of the nail coating composition;
from about 3% to about 6% by weight hydroxyethyl methacrylate based on the weight of the nail coating composition;
from about 3% to about 6% by weight hydroxypropyl methacrylate based on the weight of the nail coating composition;
from about 0.1% to about 0.4% by weight of a photoinitiator based on the weight of the nail coating composition; and
a nail art paint.

In yet other embodiments, the present invention is directed in part to radiation curable gel nail coating compositions, comprising:
from about 40% to about 60% by weight of di-[hydroxyethyl methacrylic]trimethylhexyl dicarbamate based on the weight of the nail coating composition;
from about 3% to about 6% by weight of a methacrylic acid ester based on the weight of the nail coating composition;
from about 2% to about 6% by weight hydroxyethyl methacrylate based on the weight of the nail coating composition;
from about 2% to about 6% by weight hydroxypropyl methacrylate based on the weight of the nail coating composition;
from about 0.1% to about 1% by weight of a photoinitiator based on the weight of the nail coating composition; and
from about 25 to about 40% by weight of a nail art paint based on the weight of the nail coating composition.

In some other preferred embodiments, the radiation curable gel nail coating compositions of the present invention are substantially non-aqueous, and more preferably do not contain more than a de minimis amount of water.

In certain preferred embodiments, the radiation curable gel nail coating compositions of the present invention include a polyurethane acrylate oligomer (or International Nomenclature of Cosmetic Ingredients ("INCI") designation, "Di-Hema Trimethylhexyl Dicarbamate"). The polyurethane acrylate oligomer may include monomeric, oligomeric and/or polymeric species, and any combinations thereof. In certain more preferred embodiments, the polyurethane acrylate oligomer is present at a range of from about 40% to about 60%, more preferably from about 49% to about 55%, and even more preferably at a range of from about 52% to about 53% by weight of the nail coating composition, still more preferably at a level of about 52.5%. In some alternately preferred embodiments, the polyurethane acrylate oligomer is present at a range of from about 40% to about 50%, more preferably from about 40% to about 48%, and even more preferably at a range of from about 40% to about 46% by weight of the nail coating composition. In yet other alternately preferred embodiments, the polyurethane acrylate oligomer is present at a range of from about 45% to about 55%, more preferably from about 46% to about 52% by weight of the nail coating composition.

In some other embodiments, the polyurethane acrylate oligomer is based on an alkylene isocyanate derived from an alkylene diamine, said isocyanate including but not limited to trimethylhexylene diisocyanate. Preferably, the polyurethane acrylate oligomer is derived by reaction of a hydroxyalkyl ester, preferably hydroxyethyl, more preferably 2-hydroxyethylester or hydroxypropylester, preferably 3-hydroxypropylester, or combination thereof, of an acrylic acid, preferably methacrylic acid that has been reacted with trimethylhexylene diisocyanate.

In some preferred embodiments, the radiation curable gel nail coating compositions of the present invention include an ester of methacrylic acid and an alkanol or cycloalkanol, either having one hydroxyl moiety per alkanol or cycloalkanol molecule, more preferably an isobornyl methacrylate, as a film former in the mixture. The ester is typically present at a range of from about 3% to about 5%, more preferably from about 3.5% to about 4.5%, and even more preferably at a level of about 4% by weight of the nail coating composition. Alternatively preferred, the methacrylic acid ester, preferably isobornyl methacrylate, is present at a range of from about 4% to about 6%, more preferably from about 4% to about 5% by weight of the nail coating composition. In still other preferred embodiments, the methacrylic acid ester, preferably isobornyl methacrylate, is present at a range of from about 2% to about 6%, more preferably from about 2% to about 5%, and even more preferably at a range of from about 2% to about 4% by weight of the nail coating composition.

In some preferred embodiments, the radiation curable gel nail coating compositions of the present invention include one or more esters of methacrylic acid and an alkylene diol, more preferably one of these esters is 2-hydroxyethyl methacrylate (or INCI designation, "HEMA") as a film former in the mixture, which is typically present at a range of from about 3% to about 6%, more preferably of from about 5% to about 6%, still more preferably of from about 5% to about 5.5%, and even more preferably present at a level of about 5.25% by weight of the nail coating composition. In some alternately preferred embodiments, the HEMA is present at a range of from about 2% to about 6%, more preferably from about 2% to about 5%, more preferably from about 2% to about 4% by weight of the nail coating composition.

In certain other preferred embodiments, the radiation curable gel nail coating compositions of the present invention include an ester of methacrylic acid and an alkylene diol, which is more preferably a hydroxypropyl methacrylate, still more preferably 3-hydroxypropyl methacrylate, as a film former in the mixture, which is typically present at about 3% to 6%, more preferably from about 5% to about 6%, and even more preferably at a level of about 5% by weight of the nail coating composition. In some alternately preferred embodiments, the hydroxypropyl methacrylate, preferably 3-hydroxypropyl methacrylate, is present at a range of about 2% to 6%, more preferably from about 2% to about 5%, and even more preferably at a range of from about 2% to about 4% by weight of the nail coating composition. In some particularly preferred embodiments, hydroxypropyl methacrylate, preferably 3-hydroxypropyl methacrylate, may be used in combination with 2-hydroxyethyl methacrylate.

In other preferred embodiments, the radiation curable gel nail coating compositions of the present invention include a hydroxycyclohexyl phenyl ketone as a binding agent or a photoinitiator in the mixture, which is typically present at a range of from about 0.1% to about 0.4%, still more preferably at a range of from about 0.2% to about 0.3%, and even more preferably at a level of about 0.25% by weight of the nail coating composition. In some alternately preferred embodiments, the binding agent or photoinitiator, preferably hydroxycyclohexyl phenyl ketone or benzophenone or mixture thereof, is present at a range of from about 0.1% to about 1%, still more preferably at a range of from about 0.1% to about 0.9%, still more preferably from about 0.1% to about 0.8%, and even more preferably at a range of from about 0.2% to about 0.8% by weight by weight of the nail coating composition. In other alternately preferred embodiments, the binding agent or photoinitiator, preferably hydroxycyclohexyl phenyl ketone or benzophenone or mixture thereof, is present at a range of from about 0.1% to about 0.2%, still more preferably at a range of from about 0.1% to about 0.15% by weight of the nail coating composition. In yet other alternately preferred embodiments, the binding agent or photoinitiator, preferably hydroxycyclohexyl phenyl ketone or benzophenone or mixture thereof, is present at a range of from about 0.5% to about 1%, still more preferably at a range of from about 0.6% to about 0.9%, and even more preferably at a range of from about 0.7% to about 0.8% by weight of the nail coating composition. The preferred level of the binding agent or photoinitiator is somewhat dependent on the pigments, dyes, and/or colorants color used in the nail coating compositions. While not wishing to be held to any theory or theories of operation, it is believed that darker pigments, dyes, and/or colorants used in the nail coating compositions or those pigments having relatively higher opacity characteristics require relatively higher levels of photoinitiator than compositions using lighter colors or pigments with relatively lower opacity characteristics to substantially cure the coating in an desirable time frame.

In certain other preferred embodiments, the photoinitiator included in the compositions of the present invention is other than a phosphinate, phosphine oxide, sulfanyl ketone, sulfonyl azide, polymeric morpholinoketone, alpha amino ketone or iodonium hexafluorophosphate salt.

In some preferred embodiments, for ease of manufacture, the compositions are prepared by blending a gel base formulation and a nail art paint or pigmented nail lacquer (nail polish). Nail polishes are readily available for individual ("at home") use by consumers, while nail art paints are typically prepared for commercial use rather than retail markets. The nail art paint or pigmented nail lacquer typically comprises one or more of a solvent, film former, plasticizer, crosslinking agent, colorant, suspending agent, pigment and/or dye, pH adjuster, and stability enhancer. While nail art paint and pigmented nail lacquer contain some of the same materials, the relative ratios of the contained materials typically differ. For example nail art paints are more highly pigmented than their pigmented nail lacquer counterparts. The higher level of pigment could, for example, require more suspending agent. Alternatively, the nail art paint pigments may increase the overall viscosity of the nail art paint or nail coating composition. In such systems, it may be desirable to increase solvent levels to provide increased flowability to the gel nail coating composition. It may also be desirable to add pigment stabilizing agents, such as polyester copolymers or other pigment stabilizing agents known to the skilled artisan, when higher pigment levels or less readily dispersible pigments are used in the nail art paints or nail coating compositions of the present invention to assist in providing uniform final product. Thus, in some preferred embodiments, the nail art paints or nail coating compositions containing such nail art paints further comprise polyester copolymers, such as those derived from diols, preferably branched alkylene diols, for example, neopentyl glycol, and alkane diacids, such as adipic acid, alkane polyacids, or alkane or aryl acid anhydrides, such as trimellitic anhydride.

The gel base formulation typically comprises a polyurethane acrylate oligomer, photoinitiator, and one or more esters based on methacrylic acid as disclosed herein.

In certain preferred embodiments of the nail coating compositions of the present invention the nail art paint comprises from about 3% to 5.5% by weight of a film former based on the weight of the nail coating composition. In other preferred embodiments, the nail art paint comprises up to about 0.3% by weight trimethylolpropane trimethacrylate based on the weight of the nail coating composition. In still other preferred embodiments, the nail art paint comprises from about 20% to about 40%, more preferably 20% to about 35% by weight of a solvent selected from a ketone, ester, alcohol or mixture thereof based on the weight of the nail coating composition. In yet other preferred embodiments, the nail art paint comprises from about 1% to about 2% by weight of a plasticizer based on the weight of the nail coating composition. In some other preferred embodiments, the nail art paint comprises up to about 2% by weight of pigment based on the weight of the nail coating composition.

In certain preferred embodiments of the nail coating compositions of the present invention the nail art paint comprises:
  from about 3% to 5.5% by weight of a film former based on the weight of the nail coating composition;
  up to about 0.3% by weight trimethylolpropane trimethacrylate based on the weight of the nail coating composition;
  from about 20% to about 40% by weight of a solvent selected from a ketone, ester, alcohol or mixture thereof based on the weight of the nail coating composition;
  from about 1% to about 2% by weight of a plasticizer based on the weight of the nail coating composition; and
  up to about 2% by weight of pigment based on the weight of the nail coating composition.

In certain preferred embodiments, the compositions of the present invention further comprise one or more additives known to the skilled artisan for use in the manufacture of nail polishes and/or nail coatings. Non-limiting examples of such additives include one or more solvents, film formers, plasticizers, cross-linking agents, colorants, suspending agents, pigments and/or dyes, pH adjusters, and stability enhancers.

In some other preferred embodiments, the radiation curable gel nail coating compositions of the present invention include a solvent. The choice of solvent is not critical, so long as the solvent does not substantially interfere with the irradiation and/or set or curing of the coating. The solvent may comprise a single component or may be a mixture of solvents. Typically the solvent is substantially non-aqueous. Preferably, the solvent is non-aqueous. In certain preferred embodiments, the solvent or solvents are cosmetically acceptable. By way of example, the solvents may include compounds such as esters, ketones, alcohols, alkanes, aromatics, and amides, preferably esters, ketones, and/or alcohols. In certain more preferred embodiments, the solvent is selected from butyl acetate, ethyl acetate, propyl acetate, ethanol, isopropyl alcohol, butyl alcohol, amyl acetate, acetone, and diacetone alcohol, or mixtures thereof. The combined weight percentage of solvent or solvents in the nail coating compositions are such that the solvent is typically present at a range of from about 15% to about 40%, preferably from about 18% to about 40%, more preferably about 20% to about 38%, still more preferably of from about 24% to about 38% by weight of the nail coating composition.

In certain other preferred embodiments, the radiation curable gel nail coating compositions of the present invention include a butyl acetate solvent (for example, n-butyl, isobutyl, or secondary butyl acetate or any combination thereof), preferably butyl acetate having INCI designation, "49". The butyl acetate solvent is typically present at a range of from about 5% to about 15%, preferably from about 9% to about 13%, more preferably about 11% to about 12%, still more preferably from about 11.5% to about 12%, and even more preferably at a level of about 11.75% by weight of the nail coating composition. In some alternately preferred embodiments, the butyl acetate is present at a range of from about 9% to about 20%, more preferably from about 11% to about 18%, and even more preferably at a range of from about 12% to about 17% by weight of the nail coating composition.

In certain other preferred embodiments, the radiation curable gel nail coating compositions of the present invention include a propyl acetate solvent (for example, n-propyl or isopropyl acetate or any combination thereof), preferably n-propyl acetate. The propyl acetate solvent is typically present at a range of from about 0.2% to about 1%, preferably from about 0.4% to about 0.8% by weight of the nail coating composition.

In other preferred embodiments, radiation curable gel nail coating compositions of the present invention include ethyl acetate as a solvent in the mixture, which is typically present at a range of from about 8% to about 12%, and even more preferably from about 10% to 11%, still more preferably from about 10% to about 10.5%, with a level of about 10.25% by weight of the nail coating composition being even more preferred. In some alternately preferred embodiments, the ethyl acetate is present at a range of from about 9% to about 15%, more preferably from about 10% to about 14%, and even more preferably from about 10% to about 13% by weight of the nail coating composition.

In certain preferred embodiments, the radiation curable gel nail coating compositions of the present invention include ethanol, preferably SD alcohol 40-B, a grade of specifically denatured ethanol, as a solvent in the mixture. The ethanol solvent is typically present at a range from about 1% to about 4%, preferably from about 2% to about 4%, more preferably from about 2% to 3.75%, still more preferably from about 3% to about 3.5%, and even more preferably at a level of about 3.17% by weight of the nail coating composition. In some alternately preferred embodiments, the SD alcohol is present at a range of from about 2% to about 5%, preferably from about 3% to about 4% by weight of the nail coating composition.

In certain preferred embodiments, the radiation curable gel nail coating compositions of the present invention include butyl alcohol, including n-butyl, isobutyl, and/or sec-butyl alcohol and mixtures thereof, preferably n-butyl alcohol, as a solvent in the mixture. The butyl alcohol solvent is typically present at a range from about 1% to about 6%, preferably from about 2% to about 5%, more preferably from about 2% to about 4% by weight of the nail coating composition.

In certain other preferred embodiments, the radiation curable gel nail coating compositions of the present invention include isopropyl alcohol as a solvent in the mixture, which is typically present at a range of from about 0.5% to about 1.5%, and even more preferably present at a level of about 1% by weight of the nail coating composition. In other alternately preferred embodiments, the isopropyl alcohol is present at a range of from about 0.5% to about 2%, preferably from about 1% to about 2% by weight of the nail coating composition.

In some preferred embodiments, radiation curable gel nail coating compositions of the present invention include an amyl acetate solvent, such as amyl or isoamyl acetate or combination thereof, which is typically present at a range of from about 0.5% to about 1%, preferably from about 0.6% to about 0.7%, and even more preferably present at a level of about 0.65% by weight of the nail coating composition. In some alternately preferred embodiments, the amyl acetate is present at a range of from about 0.6% to about 0.9%, preferably from about 0.6% to about 0.8% by weight of the nail coating composition.

In certain other preferred embodiments, radiation curable gel nail coating compositions of the present invention include acetone or other ketone, preferably acetone, as a solvent in the mixture. The ketone solvent is typically present at a range of from about 0.4% to about 0.5%, and even more preferably present at a level of from about 0.43% to about 0.45% by weight of the nail coating composition. In other alternately preferred embodiments, the ketone solvent is present at a level of from about 0.5% to about 1%, preferably from about 0.5% to about 0.75% by weight of the nail coating composition.

In certain preferred embodiments, the radiation curable gel nail coating compositions of the present invention include diacetone alcohol as a solvent in the mixture, which is typically present at a range of from about 0.06% to about 0.1%, and even more preferably present at a level of about 0.08% by weight of the nail coating composition. In certain alternately preferred embodiments, diacetone alcohol is present at a range of from about 0.08% to about 0.1% by weight of the nail coating composition.

In certain other preferred embodiments, the radiation curable gel nail coating compositions of the present invention include a nitrocellulose as a film former in the mixture. Nitrocellulose is typically present at a range of from about 3% to 5.5%, more preferably from about 4% to about 5%, still more preferably from about 4% to about 4.5%, and even more preferably at a level of about 4.21% by weight of the nail coating composition. In other alternately preferred embodiments, the nitrocellulose is present at a range of about 3% to 7%, more preferably from about 3% to about 6% by weight of the nail coating composition.

Alternately, the radiation curable gel nail coating compositions of the present invention may comprise other conventional film formers such as cellulose acetate, cellulose acetate butyrate, and ethyl cellulose; polyesters; resins, such as polyurethane resins, alkyd resins, and polyvinyl resins such as polyvinyl acetate, polyvinyl chloride, polyvinylbutyrate; (meth)acrylic and vinyl copolymers such as styrene/butadiene copolymers, acrylate/vinyl acetate copolymers, acrylonitrile/butadiene copolymers, and ethylene/vinyl acetate copolymers.

In certain other preferred embodiments, the radiation curable gel nail coating compositions of the present invention include a dimethicone as a film former in the mixture, which is typically present at a range of from about 0.005% to about 0.02%, more preferably from about 0.005% to about 0.01%, and even more preferably at a level of about 0.0075% by weight of the nail coating composition. In some alternately preferred embodiments, the dimethicone is present at a range of from about 0.007% to about 0.01% by weight of the nail coating composition.

In certain preferred embodiments the radiation curable gel nail coating compositions of the present invention include at least one plasticizer. Plasticizers useful in the presently claimed nail enamel composition include plasticizers commonly employed in nail varnish compositions. These plasticizers encompass, but are not limited to, dibutyl phthalate, dioctyl phthalate, tricresyl phthalate, butyl phthalate, dibutoxy ethyl phthalate, diamylphthalate, tosyl amide, N-ethyl-tosyl amide, sucrose acetate isobutyrate, camphor, castor oil, citrate esters, glyceryl diesters, glyceryl triesters, tributyl phosphate, triphenyl phosphate, butyl glycolate, benzyl benzoate, butyl acetyl ricinoleate, butyl stearate, trimethylpentanyl diisobutyrate and dibutyl tartrate.

In some other preferred embodiments, the radiation curable gel nail coating compositions of the present invention include a sucrose acetate isobutyrate as a plasticizer in the mixture, and is typically present at a range of from about 0.2% to about 1%, preferably from about 0.4% to about 0.5%, and even more preferably at a level of about 0.45% by weight of the nail coating composition. Alternately preferred in some embodiments, the sucrose acetate isobutyrate is present at a range of from about 0.45% to about 0.75%, more preferably at a level of from about 0.5% to about 0.75% by weight of the nail coating composition.

In certain preferred embodiments, the radiation curable gel nail coating compositions of the present invention include an alkyl tosylamide, preferably ethyl tosylamide, as a plasticizer in the mixture, and is typically present at a range of from about 0.4% to 0.5%, and even more preferably at a level of about 0.45% by weight of the nail coating composition. In some alternately preferred embodiments, the alkyl tosylamide is present at a range of from about 0.41% to 0.75%, more preferably from about 0.45% to 0.75%, and even more preferably from about 0.5% to about 0.6% by weight of the nail coating composition.

In some preferred embodiments, the radiation curable gel nail coating compositions of the present invention include camphor as a plasticizer in the mixture. Camphor is typically present at a range of from about 0.25% to about 0.35%, and even more preferably at a level of about 0.28% by weight of the nail coating composition. In some alternately preferred embodiments, the camphor is present at a range of from about 0.2% to about 0.5%, more preferably from about 0.2% to about 0.4% by weight of the nail coating composition.

In some other preferred embodiments, the radiation curable gel nail coating compositions of the present invention include trimethylpentanyl diisobutyrate as a plasticizer in the mixture, and is typically present at a range of from about 0.2% to about 1%, preferably from about 0.3% to about 0.9%, and even more preferably at a level of from about 0.4% to about 0.8% by weight of the nail coating composition.

In certain other preferred embodiments, the radiation curable gel nail coating compositions of the present invention include triphenyl phosphate as a plasticizer in the mixture, and is typically present at a range of from about 0.2% to about 1%, preferably from about 0.3% to about 0.9%, and even more preferably at a level of from about 0.4% to about 0.8% by weight of the nail coating composition.

In some preferred embodiments, the radiation curable gel nail coating compositions of the present invention include one or more cross-linking agents. Typically, these cross-linking agents are esters of a polyhydroxy compound and methacrylic acid, wherein a substantial number of the hydroxy groups of the polyhydroxy compound, and preferably each of the hydroxy groups, have been esterified with methacrylic acid. The polyhydroxy compounds preferably have 3 or more hydroxy groups per molecule, more preferably 3 or 4 hydroxy groups, still more preferably 3 hydroxy groups per molecule of polyhydroxy compound. In certain yet more preferred embodiments, the cross-linking agent is trimethylolpropane trimethacrylate ("TMPTA"). The cross-linking agent is typically present at a range of from about 0.15% to about 0.35%, more preferably from about 0.2% to about 0.3%, still more preferably from about 0.25% to about 0.29%, and even more preferably at a level of about 0.29% by weight of the nail coating composition. In some alternately preferred embodiments, the cross-linking agent is present at a level of from about 0.2% to about 0.5%, preferably from about 0.2% to about 0.4% by weight of the nail coating composition.

In still other preferred embodiments, the radiation curable gel nail coating compositions of the present invention include a colorant, preferably D&C Violet #2. The D&C Violet #2 is typically present at a range of from about 0.1% to about 0.4%, and even more preferably at a level of about 0.15% by weight of the nail coating composition. In other alternately preferred embodiments, the D&C Violet #2 is present at a range of from about 0.1% to about 0.3%, more preferably from about 0.1% to about 0.2% by weight of the nail coating composition. In certain preferred embodiments, the D&C Violet #2 is contained in the gel base component of the nail coating compositions.

In yet other preferred embodiments, radiation curable gel nail coating compositions of the present invention include a suspending agent in the mixture, preferably stearalkonium hectorite. The suspending agent is typically present at a range of from about 0.03% to about 0.07%, and even more preferably at a level of about 0.05% by weight of the nail coating composition. In other alternately preferred embodiments, the suspending agent, preferably stearalkonium hectorite, is present at a range of from about 0.05% to about 0.07% by weight of the nail coating composition.

In some preferred embodiments, the radiation curable gel nail coating compositions of the present invention include one or more pigments or dyes that may vary in color that may function as colorants in the mixture, and which may be present at a range of from about 0.01% to about 0.05%, preferably from about 0.03 to about 0.04%, and even more preferably at a level of about 0.035% by weight of the nail coating composition. Typically, these pigments are present in the nail lacquer or nail art paint component of the compositions of the present invention. In certain other alternately preferred embodiments, the one or more pigments or dyes may be present at a range of from about 0.01% to about 2%, still more preferably at a range of from about 0.1% to about 2%, and even more preferably at a range of from about 0.5% to about 2% by weight of the nail coating composition. Non-limiting examples of pigments useful in the compositions of the present invention include Titanium Dioxide, Black Iron Oxide, D&C Black #2, FD&C Red #4, D&C Red #6, D&C Red #7, D&C Red #17, D&C Red #21, D&C Red #22, D&C Red #27, D&C Red #28, D&C Red #30, D&C Red #31, D&C Red #33, D&C Red #34, D&C Red #36, D&C Red #40, FD&C Blue #1, D&C Orange #4, D&C Orange #5, D&C Orange #10, D&C Orange #11, D&C Blue #4, D&C Brown #1, FD&C Green #3, D&C Green #5, D&C Green #6, D&C Green #8, FD&C Yellow #5, FD&C Yellow #6, D&C Yellow #7, D&C Yellow #8, D&C Yellow #10, and D&C Yellow #11 and combinations thereof. In certain preferred embodiments, the pigments are contained in the pigmented lacquer or nail art paint component of the nail coating compositions.

In other preferred embodiments, the radiation curable gel nail coating compositions of the present invention include a pH adjuster in the mixture, preferably phosphoric acid, which is typically present at a range of from about 0.02% to about 0.04%, and even more preferably present at a level of about 0.03% by weight of the nail coating composition. Alternately preferred, the pH adjuster is present at a range of from about 0.03% to about 0.04% by weight of the nail coating composition.

In certain preferred embodiments, the radiation curable gel nail coating compositions of the present invention include a stability enhancer, preferably citric acid, which is typically present at a range of from about 0.005% to about 0.02%, more preferably at a range of from about 0.005% to about 0.01%, and even more preferably at a level of about 0.0075% by weight of the nail coating composition. In some alternately preferred embodiments, the citric acid is present at a range of from about 0.0075% to about 0.01% by weight of the nail coating composition.

In other preferred embodiments, the radiation curable gel nail coating compositions of the present invention further comprise less than about 1% by weight of urethane resin bisphenol A diglycidyl methacrylate ("BISGMA", in polymeric, oligomeric and/or monomeric form); more preferably less than about 0.5% of based on the weight of the nail coating composition. In certain other more preferred embodiments, the radiation curable gel nail coating compositions of the present invention do not contain BISGMA urethane resin. The BISGMA based urethane resin is reportedly prepared by reacting the hydroxyl functions of BISGMA with a hydrocarbon diisocyanate. (BISGMA can be purchased from Esstech, and is sold as Nupol 46-4005 from Cook Composites and Polymers). See Lilley et al., U.S. Pat. No. 6,803,394, the disclosure of which is hereby incorporated herein by reference, in its entirety.

In certain preferred embodiments, the radiation curable gel nail coating compositions of the present invention is capable of being directly applied to a nail (natural nail or synthetic nail or nail extension. That is, some of the compositions may be applied without the need to first apply a solvent evaporation basecoat to the nail.

In still other preferred embodiments, the radiation curable gel nail coating compositions of the present invention further comprise one or more additives, wherein the additive(s) are other than maleimide functional materials, such as for example, hydroxy ethylmaleimide, triethylene glycol biscarbonate bisethylmaleimide, 2-isopropyl urethane ethylmaleimide, 2-acryloyl ethylmaleimide, acetoxy ethyl maleimide, isophorone bisurethane bisethylmaleimide, N,N'-hexamethylenebismaleimide, and/or N,N'-(2,2,4-trimethylhexamethylene)-bismaleimide.

In some particularly preferred embodiments, the nail coating compositions have the following formulations, Formulation 1, 2, 3 or 4:

| Formulation 1 | |
|---|---|
| Ingredients | Wt. % range |
| Di-Hema Trimethylhexyl Dicarbamate | 49.00-55.00 |
| Butyl Acetate | 9.00-13.00 |
| Ethyl Acetate | 8.00-12.00 |
| Isobornyl Methacrylate | 4.00-6.00 |
| HEMA | 3.00-6.00 |
| Hydroxypropyl Methacrylate | 3.00-6.00 |
| Nitrocellulose | 3.00-5.50 |

Formulation 1

| Ingredients | Wt. % range |
| --- | --- |
| SD Alcohol 40-B | 2.00-3.75 |
| Isopropyl Alcohol | .50-1.50 |
| Amyl Acetate | .60-.70 |
| Sucrose Acetate Isobutyrate | .40-.50 |
| Ethyl Tosylamide | .40-.50 |
| Acetone | .40-.50 |
| Camphor | .25-.35 |
| Trimethylpropane Trimethacrylate | .22-.29 |
| Violet 2/CI 60725 | <0.4 |
| Hydroxycyclohexyl phenyl ketone | <0.3 |
| Diacetone Alcohol | .06-.10 |
| Stearalkonium Hectorite | .03-.07 |
| Pigment(s) or Dye(s) | .01-2.0 |
| Phosphoric Acid | .02-.04 |
| Citric Acid | <.02 |
| Dimethicone | <.02 |

Formulation 2

| Ingredients | Wt. % range |
| --- | --- |
| Di-Hema Trimethylhexyl Dicarbamate | 44.00-55.00 |
| Butyl Acetate | 9.00-17.00 |
| Ethyl Acetate | 8.00-13.00 |
| Isobornyl Methacrylate | 3.00-6.00 |
| HEMA | 2.00-6.00 |
| Hydroxypropyl Methacrylate | 2.00-6.00 |
| Nitrocellulose | 3.00-5.75 |
| SD Alcohol 40-B | 2.00-4.00 |
| Isopropyl Alcohol | .50-1.75 |
| Amyl Acetate | .60-.85 |
| Sucrose Acetate Isobutyrate | .40-.75 |
| Ethyl Tosylamide | .40-.75 |
| Acetone | .40-.75 |
| Camphor | .25-.40 |
| Trimethylpropane Trimethacrylate | .22-.40 |
| Violet 2/CI 60725 | <0.4 |
| Hydroxycyclohexyl phenyl ketone | <1.0 |
| Diacetone Alcohol | .06-.10 |
| Stearalkonium Hectorite | .03-.07 |
| Pigment(s) or Dye(s) | .01-2.0 |
| Phosphoric Acid | .02-.04 |
| Citric Acid | <.02 |
| Dimethicone | <.02 |

Formulation 3

| Ingredients | Wt. % range |
| --- | --- |
| Polyurethane Acrylate Oligomer | 49.00-55.00 |
| Butyl Acetate | 9.00-13.00 |
| Ethyl Acetate | 8.00-12.00 |
| 2-Hydroxyethyl Methacrylate | 3.00-6.00 |
| Hydroxypropyl Methacrylate | 3.00-6.00 |
| Nitrocellulose | 3.00-5.50 |
| Isobornyl Methacrylate | 3.00-5.00 |
| SD Alcohol 40-B | 2.00-3.75 |
| Isopropyl Alcohol | .50-1.50 |
| Amyl Acetate | .60-.70 |
| Sucrose Acetate Isobutyrate | .40-.50 |
| Ethyl Tosylamide | .40-.50 |
| Acetone | .40-.50 |
| Camphor | .25-.35 |
| Hydroxycyclohexyl phenyl ketone | <0.4 |
| D&C Violet #2 | <0.4 |
| Diacetone Alcohol | .06-.10 |
| Stearalkonium Hectorite | .03-.07 |
| Pigment(s) or Dye(s | .01-.05 |
| Phosphoric Acid | .02-.04 |
| Citric Acid | <.02 |
| Dimethicone | <.02 |

Formulation 4

| Ingredients | Wt. % range |
| --- | --- |
| Polyurethane Acrylate Oligomer | 40-48 |
| Butyl Acetate | 11-18 |
| Ethyl Acetate | 10-14 |
| 2-Hydroxyethyl Methacrylate | 2-4 |
| Hydroxypropyl Methacrylate | 2-4 |
| Nitrocellulose | 3-6 |
| Polymeric Nail Art Paint Stabilizer | 2-4 |
| Isobornyl Methacrylate | 2-5 |
| Butyl Alcohol | 2-5 |
| Isopropyl Alcohol | 1-2 |
| Trimethylpenanyl Diisobutyrate | 0.2-1 |
| Triphenyl phosphate | .02-1 |
| Propyl Acetate | 0.4-0.8 |
| Hydroxycyclohexyl phenyl ketone/ Benzophenone | 0.2-1 |
| D&C Violet #2 | 0.1-0.4 |
| Diacetone Alcohol | 0.06-.10 |
| Stearalkonium Hectorite | 0.03-0.07 |
| Pigment(s) or Dye(s | .01-2 |
| Phosphoric Acid | .02-.04 |
| Citric Acid | <.02 |
| Dimethicone | <.02 |

The compositions according to the invention may also include one or more additives recognized by a person skilled in the art as being capable of incorporation into such nail coating compositions. For example, the composition may include at least one cosmetically active compound, which may be selected from vitamins, minerals, moisturizers, hardening agents such as silica and formaldehyde/glyoxal, UV absorbers, and fibers such as nylon or aramide fibers. Additional additive ingredients may include keratin and its derivatives, melanin, collagen, cysteine, chitosan and its derivatives, ceramides, biotin, oligoelements, protein hydrolysates, and phospholipids.

A person skilled in the art can, without undue experimentation, select those optional additional compounds and/or their quantity, so that the advantageous properties of the composition according to the invention are not, or are not substantially, impaired by the inclusion of such additives.

The compositions according to the invention may be prepared by a person skilled in the art on the basis of his or her general knowledge and according to the state of the art.

The compositions according to the invention are also useful in the kits and or methods of use of the present invention.

The invention will be further clarified by the following examples, which are intended to be illustrative of the invention, but not limiting thereof.

Typical Method of Blending a Nail Polish and a Gel Base

While all of the components of the pigmented lacquer and gel may be individually formulated into a final product, it is preferable in some embodiments to blend a previously prepared pigmented lacquer (i.e., nail polish) with a gel formulation. By way of general guidance, the gel formulation and lacquer are blended together using any stirring or mixing equipment capable of providing general mixing for a time and under conditions to adequately blend the lacquer and gel formulation. Typically a time of 0.5 to 3 hours is sufficient, preferably from about 0.5 to about 1 hour, more preferably 30 to 50 minutes. As a general rule the mixture can be heated to any temperature that facilitates the blending operation while maintaining the stability of the components, lacquers or formulations. For example, the combination of components may be heated to about 30 to about 150 degrees Fahrenheit, more preferably about 50 to about 130 degrees Fahrenheit, still more preferably form about 80 to about 110 degrees Fahrenheit. While the preferred ratio of lacquer to gel in the compositions does depend to some extent upon the lacquer chosen, the ratio typically falls within the range of about 35 to 45 volume parts, more preferably about 39 to 41 parts of lacquer to about 100 parts of gel formulation.

In similar manner to the pigmented lacquers, nail art paints may be blended with gel bases as disclosed hereinabove to provide certain of the final product gel coating compositions. While the preferred ratio of nail art paint to gel in the compositions does depend to some extent upon the nail art paint chosen, the ratio typically falls within the range of from about 40% to about 60% by weight parts, more preferably about 45% to about 55% by weight of the gel base component (i.e., component including polyurethane acrylate oligomer, methacrylate ester, any monoesters of methacrylic acid and a diol, and photoinitiator) based on the weight of the final nail coating composition.

Example 1

Hypothetical Procedure for Blending Pigmented Lacquer and Gel Base

A previously prepared pigmented lacquer (such as a commercially available nail polish) is blended with a gel formulation of the present invention (typical gel formulation shown below) in a ratio of 40 parts by volume of lacquer to 100 parts by volume of gel formulation, The blend is heated to approximately 110 degrees F. The mixture is slowly stirred for approximately 40 minutes, and allowed to cool for approximately 2 hours. Once cooled, the mixture is preferably deposited into UV coated bottles.

Example 2

Hypothetical Procedure for Blending Nail Art Paint and Gel Base

A previously prepared nail art paint [butyl acetate (16.5 parts), ethyl acetate (13 parts), nitrocellulose (5.75 parts), butyl alcohol (4 parts), polymeric nail art paint stabilizer (3 parts), isopropyl alcohol (1.75 parts), trimethylpentanyl diisobutyrate (0.75 parts), triphenyl phosphate (0.75 parts), propyl acetate (0.75 parts), diacetone alcohol (0.1 parts), stearalkonium hectorite (0.07 parts), titanium dioxide/black iron oxide (0.09 parts), phosphoric acid (0.04 parts), citric acid (0.01 parts), dimethicone (0.01 parts), benzophenone (0.01 parts), and D&C Yellow #11 (0.07 parts)] is blended with a gel formulation of the present invention [(Di-Hema Trimethylhexyl Dicarbamate oligomer (44.5 parts by weight), Isobornyl Methacrylate (3.25 parts by weight), HEMA (2.5 parts by weight), Hydroxypropyl Methacrylate (2.25 parts by weight), Violet 2/CI-60725 (0.1 parts by weight), Hydroxycyclohexyl phenyl ketone/benzophenone (0.75 parts by weight)]. The blend is heated to approximately 110 degrees F. The mixture is slowly stirred for approximately 40 minutes, and allowed to cool for approximately 2 hours. Once cooled, the mixture is preferably deposited into UV coated bottles.

When any variable occurs more than one time in any formula, its definition in each occurrence is independent of its definition at every other occurrence. Combinations of variables are permissible only if such combinations result in stable formulations.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way.

When ranges are used herein for physical properties, elements or variables in formula compositions, percent composition of elements or variables in formulas, all combinations and subcombinations of ranges and specific embodiments therein are intended to be included. Unless otherwise indicated, % ranges for components are expressed on a volume per total volume basis. For example, if ethyl acetate is used as a solvent at 10%, then the ethyl acetate volume added is equal to 10% of the total volume of the blended product formulation.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

[Embodiment 1]

A radiation curable gel nail coating composition, comprising:
  from about 40% to about 60% by weight of di-[hydroxyethyl methacrylic]trimethylhexyl dicarbamate based on the weight of the nail coating composition;
  from about 3% to about 5% by weight by weight of at least one methacrylic acid ester based on the weight of the nail coating composition;
  from about 3% to about 6% by weight hydroxyethyl methacrylate based on the weight of the nail coating composition;
  from about 3% to about 6% by weight hydroxypropyl methacrylate based on the weight of the nail coating composition;
  from about 0.1% to about 0.4% by weight of a photoinitiator based on the weight of the nail coating composition; and
  a pigmented nail lacquer.

[Embodiment 2]

A radiation curable gel nail coating composition, comprising:
  from about 40% to about 60% by weight of di-[hydroxyethyl methacrylic]trimethylhexyl dicarbamate based on the weight of the nail coating composition;
  from about 3% to about 6% by weight of at least one methacrylic acid ester based on the weight of the nail coating composition;
  from about 2% to about 6% by weight hydroxyethyl methacrylate based on the weight of the nail coating composition;

from about 2% to about 6% by weight hydroxypropyl methacrylate based on the weight of the nail coating composition;
from about 0.1% to about 0.4% by weight of a photoinitiator based on the weight of the nail coating composition; and
a nail art paint.

[Embodiment 3]
radiation curable gel nail coating composition, comprising:
from about 40% to about 60% by weight of di-[hydroxyethyl methacrylic]trimethylhexyl dicarbamate based on the weight of the nail coating composition;
from about 3% to about 6% by weight of a methacrylic acid ester based on the weight of the nail coating composition;
from about 2% to about 6% by weight hydroxyethyl methacrylate based on the weight of the nail coating composition;
from about 2% to about 6% by weight hydroxypropyl methacrylate based on the weight of the nail coating composition;
from about 0.1% to about 1% by weight of a photoinitiator based on the weight of the nail coating composition; and
from about 25% to about 40% by weight of a nail art paint based on the weight of the nail coating composition.

[Embodiment 4]
A radiation curable gel nail coating composition according to embodiment 3, wherein:
the hydroxyethyl methacrylate is present at a level of from about 2.5% to about 4% by weight based on the weight of the nail coating composition; and
the hydroxypropyl methacrylate is present at a level of from about 2.25% to about 5% by weight based on the weight of the nail coating composition.

[Embodiment 5]
A radiation curable gel nail coating composition according to any one of embodiments 2, 3, and 4, wherein the photoinitiator is present at a level of from about 0.5% to about 1% by weight based on the weight of the nail coating composition.

[Embodiment 6]
A radiation curable gel nail coating composition according to any one of embodiments 2, 3, 4, and 5, wherein the nail art paint comprises:
from about 3% to 6% by weight of a film former based on the weight of the nail coating composition;
up to about 0.4% by weight trimethylolpropane trimethacrylate based on the weight of the nail coating composition;
from about 20% to about 38% by weight of a solvent selected from a ketone, ester, alcohol or mixture thereof based on the weight of the nail coating composition;
from about 1% to about 2% by weight of a plasticizer based on the weight of the nail coating composition; and
up to about 2% by weight of pigment based on the weight of the nail coating composition.

[Embodiment 7]
A radiation curable gel nail coating composition according to any one of embodiments 1 to 6, wherein the film former is selected from nitrocellulose and dimethicone, or a mixture thereof.

[Embodiment 8]
A radiation curable gel nail coating composition according to any one of embodiments 1 to 7, wherein the solvent is selected from isopropyl alcohol, ethanol, diacetone alcohol, ethyl acetate, butyl acetate, amyl acetate, acetone, or a mixture thereof.

[Embodiment 9]
A radiation curable gel nail coating composition according to any one of embodiments 1 to 8, wherein the plasticizer is selected from sucrose acetate isobutyrate, ethyl tosylamide, and camphor, or a mixture thereof.

[Embodiment 10]
A radiation curable gel nail coating composition according to any one of embodiments 1 to 9, wherein the photoinitiator is hydroxycyclohexyl phenyl ketone.

[Embodiment 11]
A radiation curable gel nail coating composition according to any one of embodiments 1 to 10, wherein the methacrylic acid ester is isobornyl methacrylate.

[Embodiment 12]
A radiation curable gel nail coating composition according to any one of embodiments 1 to 11, wherein the di-[hydroxyethyl methacrylic]trimethylhexyl dicarbamate is present at from about 44% to about 52% by weight of the nail coating composition.

[Embodiment 13]
A radiation curable gel nail coating composition according to any one of embodiments 1 to 12, wherein the composition is capable of being cured by UV irradiation.

[Embodiment 14]
A kit suitable for coating mammalian nails with a radiation curable gel nail coating composition, comprising:
a radiation curable gel nail coating composition according to any one of embodiments 1 to 13; and
a bottle designed to substantially exclude the passage of UV light.

[Embodiment 15]
A kit according to embodiment 14, wherein the bottle comprises clear glass coated with a finish to substantially exclude UV light transmission through the glass.

[Embodiment 16]
A kit according to any one of embodiments 14 and 15, further comprising a brush for applying the radiation curable gel nail coating composition.

[Embodiment 17]
A method of coating mammalian nails with a radiation curable gel nail coating composition, wherein the method comprises:
applying a nail coating composition according to any one of embodiments 1 to 13 to a mammalian nail; and
radiation curing the composition on the nail.

What is claimed is:
1. A radiation curable gel nail coating composition, comprising:
from about 40% to 58% by weight of di-[hydroxyethyl methacrylic] trimethylhexyl dicarbamate based on the weight of the radiation curable gel nail coating composition;
from about 3% to 4% by weight of at least one methacrylic acid ester based on the weight of the radiation curable gel nail coating composition;
from about 3% to 4% by weight by weight hydroxyethyl methacrylate based on the weight of the radiation curable gel nail coating composition;
from about 3% to 4% by weight hydroxypropyl methacrylate based on the weight of the radiation curable gel nail coating composition;
from about 0.1% to about 0.4% by weight of a photoinitiator based on the weight of the radiation curable gel nail coating composition; and
a nail art paint.
2. A radiation curable gel nail coating composition, comprising:

from about 40% to 58% by weight of di-[hydroxyethyl methacrylic] trimethylhexyl dicarbamate based on the weight of the radiation curable gel nail coating composition;

from about 3% to 4% by weight of a methacrylic acid ester based on the weight of the radiation curable gel nail coating composition;

from about 2% to 4% by weight hydroxyethyl methacrylate based on the weight of the radiation curable gel nail coating composition;

from about 2% to 4% by weight hydroxypropyl methacrylate based on the weight of the radiation curable gel nail coating composition;

from about 0.1% to about 1% by weight of a photoinitiator based on the weight of the radiation curable gel nail coating composition; and from about 25 to about 40% by weight of a nail art paint based on the weight of the radiation curable gel nail coating composition.

3. A radiation curable gel nail coating composition according to claim 2, wherein the nail art paint comprises:

from about 3% to 6% by weight of a film former based on the weight of the radiation curable gel nail coating composition;

up to about 0.4% by weight trimethylolpropane trimethacrylate based on the weight of the radiation curable gel nail coating composition;

from about 20% to about 38% by weight of a solvent selected from a ketone, ester, alcohol or mixture thereof based on the weight of the radiation curable gel nail coating composition;

from about 1% to about 2% by weight of a plasticizer based on the weight of the radiation curable gel nail coating composition; and up to about 2% by weight of pigment based on the weight of the radiation curable gel nail coating composition.

4. A radiation curable gel nail coating composition according to claim 3, wherein the photoinitiator is hydroxycyclohexyl phenyl ketone.

5. A radiation curable gel nail coating composition according to claim 4, wherein the film former is selected from nitrocellulose and dimethicone, or a mixture thereof.

6. A radiation curable gel nail coating composition according to claim 5, wherein the solvent is selected from isopropyl alcohol, ethanol, diacetone alcohol, ethyl acetate, butyl acetate, amyl acetate, acetone, or a mixture thereof.

7. A radiation curable gel nail coating composition according to claim 6, wherein the plasticizer is selected from sucrose acetate isobutyrate, ethyl tosylamide, and camphor, or a mixture thereof.

8. A radiation curable gel nail coating composition according to claim 7, wherein the methacrylic acid ester is isobornyl methacrylate.

9. A radiation curable gel nail coating composition according to claim 8, wherein the di-[hydroxyethyl methacrylic] trimethylhexyl dicarbamate is present at from about 44% to about 52% by weight of the radiation curable gel nail coating composition.

10. A radiation curable gel nail coating composition according to claim 9, wherein the hydroxyethyl methacrylate is present at a level of from about 2.5% to 4% by weight based on the weight of the radiation curable gel nail coating composition; and the hydroxypropyl methacrylate is present at a level of from about 2.25% to 4% by weight based on the weight of the radiation curable gel nail coating composition.

11. A radiation curable gel nail coating composition according to claim 10, wherein the photoinitiator is present at a level of from about 0.5% to about 1% by weight based on the weight of the radiation curable gel nail coating composition.

12. A radiation curable gel nail coating composition according to claim 11, wherein the composition is capable of being cured by UV irradiation.

13. A kit suitable for coating mammalian nails with a radiation curable gel nail coating composition, comprising:

a radiation curable gel nail coating composition according to claim 2; and a bottle designed to substantially exclude the passage of UV light.

14. A kit according to claim 13, wherein the bottle comprises clear glass coated with a finish to substantially exclude UV light transmission through the glass.

15. A kit according to claim 13, further comprising a brush for applying the radiation curable gel nail coating composition.

16. A method of coating mammalian nails with a radiation curable gel nail coating composition, wherein the method comprises:

applying a nail coating composition according to claim 2 contiguously to a mammalian nail; and radiation curing the composition on the nail.

17. A radiation curable gel nail coating composition, comprising:

from about 40% to 58% by weight of di-[hydroxyethyl methacrylic] trimethylhexyl dicarbamate based on the weight of the radiation curable gel nail coating composition;

from about 3% to 4% by weight of at least one methacrylic acid ester based on the weight of the radiation curable gel nail coating composition;

from about 3% to 4% by weight hydroxyethyl methacrylate based on the weight of the radiation curable gel nail coating composition;

from about 3% to 4% by weight hydroxypropyl methacrylate based on the weight of the radiation curable gel nail coating composition from about 0.1% to about 0.4% by weight of a photoinitiator based on the weight of the radiation curable gel nail coating composition; and a pigmented nail lacquer.

* * * * *